United States Patent [19]

Cosman

[11] 4,385,636

[45] * May 31, 1983

[54] TELEMETRIC DIFFERENTIAL PRESSURE SENSOR WITH THE IMPROVEMENT OF A CONDUCTIVE SHORTED LOOP TUNING ELEMENT AND A RESONANT CIRCUIT

[76] Inventor: Eric R. Cosman, 872 Concord Ave., Belmont, Mass. 02178

[*] Notice: The portion of the term of this patent subsequent to Aug. 4, 1998, has been disclaimed.

[21] Appl. No.: 231,707

[22] Filed: Feb. 5, 1981

Related U.S. Application Data

[60] Division of Ser. No. 908,615, May 23, 1978, abandoned, which is a continuation-in-part of Ser. No. 697,951, Apr. 13, 1978, abandoned, which is a continuation-in-part of Ser. No. 697,948, Apr. 13, 1978, abandoned.

[51] Int. Cl.$^3$ .............................................. A61B 5/10
[52] U.S. Cl. ................................. 128/748; 128/660
[58] Field of Search ..................... 128/748, 673–675, 128/630, 645–652, 660

[56] References Cited

U.S. PATENT DOCUMENTS

| | | | |
|---|---|---|---|
| 3,703,099 | 11/1972 | Rouse | 73/398 AR |
| 3,831,588 | 8/1974 | Rindner | 128/675 |
| 4,026,276 | 5/1977 | Chubbuck | 128/748 |
| 4,062,354 | 12/1977 | Taylor et al. | 128/748 |
| 4,114,606 | 9/1978 | Seylar | 128/748 |
| 4,127,110 | 11/1978 | Bullara | 128/748 |
| 4,265,252 | 5/1981 | Chubbuck et al. | 128/748 |
| 4,281,666 | 8/1981 | Cosman | 128/748 |

Primary Examiner—Lee S. Cohen
Assistant Examiner—Angela D. Sykes
Attorney, Agent, or Firm—Richard J. Birch

[57] ABSTRACT

An improvement in design of an implantable telemetric differential pressure sensing device enabling thinner, more compact, and simplified construction for the device; increased pressure sensitivity and range of measurement; and a wider class of applications for such pressure sensing devices in diagnostic medicine and clinical monitoring. The implanted device includes a thin, planar, closed, conductive loop which moves with a flexible diaphragm, the diaphragm moving upon changes in the difference of two bodily pressures on its opposite sides. The position of the conductive loop relative to a resonant circuit fixed in the device determines the resonant frequency of the resonant circuit. The resonant frequency is detected telemetrically outside the body, and its value is used to determine the difference in the two bodily pressures.

9 Claims, 23 Drawing Figures

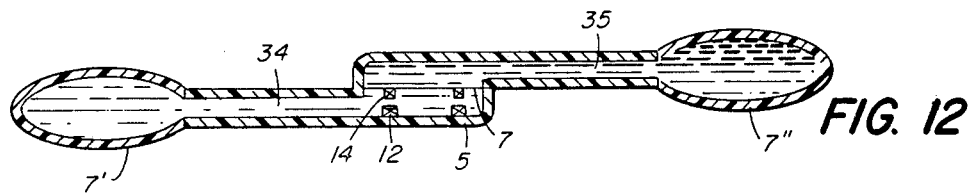
FIG. 12
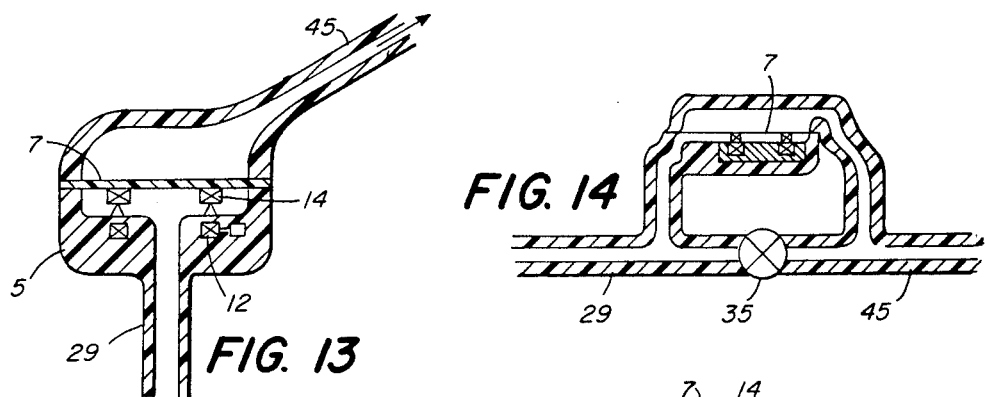
FIG. 13
FIG. 14
FIG. 15
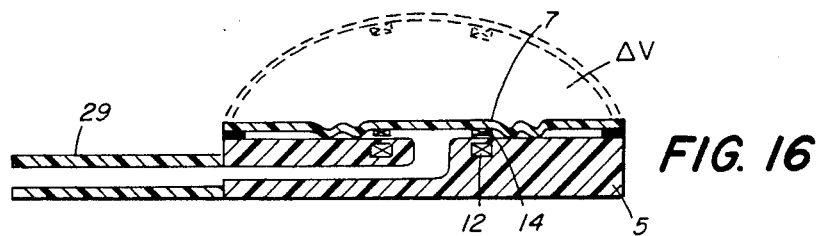
FIG. 16
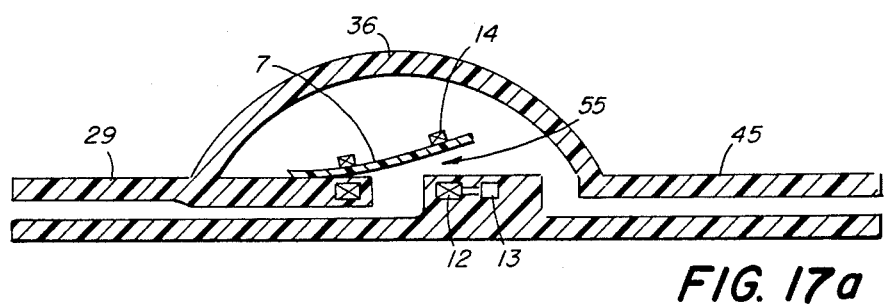
FIG. 17a

TELEMETRIC DIFFERENTIAL PRESSURE SENSOR WITH THE IMPROVEMENT OF A CONDUCTIVE SHORTED LOOP TUNING ELEMENT AND A RESONANT CIRCUIT

BACKGROUND OF THE INVENTION

The present application is a division of application Ser. No. 908,615 filed May 23, 1978, now abandoned, which is in turn a continuation-in-part of my copending patent applications Ser. Nos. 697,951 and 697,948 now abandoned, patent applications filed Apr. 13, 1978.

The present invention relates to telemetric differential pressure sensing devices that are implantable in the living body as are described in the above patent applications. In those applications, a magnetic tuning element or a conductive tuning element is attached to a diaphragm or diaphragms in the device, and the material moved relative to the coil of a resonant L-C circuit in the device as pressures on opposite sides of the diaphragm change. This motion changes the inductance of the coil which in turn changes the resonant frequency of the resonant circuit, the resonant frequency being detected telemetrically outside the body and related to the pressure difference across the diaphragm. Many design variants of this type of device and variants in the methods of using such a device to measure a bodily pressure and calibrate the device in vivo are generally explained in the above patent applications.

There are several practical difficulties in successfully implementing such devices in the real clinical situation. Of great importance is reducing the size of the implant for use in measuring intracranial pressure, and especially pressures inside hydrocephalus shunt systems which are most commonly implanted in infants. Using a magnetic slug as the tuning element requires a substantial length of the slug to achieve reasonable resonant frequency versus pressure sensitivity and a substantial diameter of the slug and coil to achieve sufficient telemetric coupling to the detector outside the body. Both these factors produce a device which is 5 mm or more in thickness, and this produces an undesirably large bump under the patient's skin if used in a standard shunt valve system. Such a bump is not only cosmetically undesirable, but it can cause irritation and even necrosis of the skin above, especially in infants, and can perturb the accuracy of a differential pressure sensor that relies on accurate transmission of pressures across the scalp. Using a conductive material can circumvent the size problem just mentioned, but standard shaped conductors such as slugs or disks characteristically worsen the Q value of the resonant circuit to the point that the resonant frequency is ill-defined and the telemetric coupling across the skin is destroyed. Also, volumetric tuning slugs, either magnetic or conductive, have an appreciable weight which causes errors in the pressure reading according to orientation of the device and causes a slower dynamic response because of their substantial inertial mass. Furthermore, such slugs are difficult to secure reliably to a fragile flexible diaphragm and to align on a coaxial geometry with respect to the coil when the common cylindrical geometry used. These factors produce a critical assembly, a less reliable sensor, and a complex diaphragm structure which is not of a thin, planar geometry. Further yet, the displacement range of a magnetic or solid conductive slug within the coil over which a reasonably large frequency shift versus displacement or pressure change can be achieved is limited to the immediate vicinity of the resonant circuit coil, and this limits the range of high sensitivity of a moving diaphragm. This in turn prohibits the design of certain types of special purpose devices such as quantitative pressure and volume sensing chambers as will be described later in this application. Still further, the mass of conventional induction tuning elements, either magnetic or conductive, makes it impossible to design a practical, ultrasensitive pressure gradient sensor as, for example, would be very useful in sensing the slow flow of cerebrospinal fluid in a hydrocephalus shunt valve or for sensing the motion under very weak pressure changes of a fragile value mechanism itself.

Accordingly, some of the principal objectives of the present design improvements are the following:

(1) To provide an extremely thin induction tuning elemement for varying the inductance of the reasonant circuit, so that very low profile sensors can be made. For a sensor in a hydrocephalus shunt system to be used between the scalp and skull of an infant, a thickness of 4 mm or less is necessary to prevent skin necrosis and prevent pressure reading errors;

(2) To provide as small a diameter sensor as possible, which means that the diameter of the resonant circuit's inductor and the associated tuning element must be minimized;

(3) To achieve a maximum sensitivity of the resonant circuit's frequency change versus diaphragm movement in order to maximize accuracy of pressure measurements and to minimize the displacements of the diaphragm as the measurements are made;

(4) To maintain a high Q-value of the resonant circuit so as to maintain a high accuracy in measurement of the reasonant frequency shifts and to maintain adequate telemetric coupling of the external detection equipment to the implanted sensor;

(5) To achieve a planar geometry of tuning element, diaphragm, and resonant circuit rather than a cumbersom cylindrical geometry which makes assembly and alignment critical;

(6) To achieve an ultra light-weight tuning element wich produces no gravitational inaccuracies, poses no inertial reaction time sluggishness, and, very importantly, enables the construction of ultra sensitive pressure vanes which can sense minute pressure gradients and slow flow of fluids in a shunt valve system, this is heretofore an impossible achievement.

(7) To provide a tuning element that will increase the range of displacements of the diaphragm relative to resonant circuit and still maintain a sensitive resonant frequency shift versus displacement curve; this would allow construction of certain quantitative pressure and volume sensitive reservoirs which are heretofore impossible to be built; and, (8) To generally simplify the moving diaphragm structure in the sense of making it a single moving structure with a minimum of component parts, a durable and robust structure preferably of a medical grade silicone rubber, and a very thin diaphragm with no bulky masses attached to it.

It should be noted here that, if one chooses, as has been attempted by several inventors in the past, to tune the capacitance of a resonant L-C circuit instead of the inductance, one would achieve many of the above features by simply making the diaphragm one side of a pressure sensitive capacitor. This however has the insurmountable failing that the capacitance of such a device is dependent on the dielectric constant between capacitor plates and in the ionic solution environment of living body there is no way of stabilizing that parameter. Thus tuning of the inductor of the L-C circuit is the only practical approach considered in this patent.

SUMMARY OF THE INVENTION

The above objects and advantages are achieved by the present design improvement which is described in the following brief summary:

A conductive tuning element of a specific geometric type is attached to or part of the diaphragm. In a simple form, a shorted or closed loop of highly conductive metal is used, the shorted loop having a planar geometry and a through opening or enclosed area which is coaxial and of about the same shape and size as the inductive coil in the resonant L-C circuit of the implanted device. The loop moves with the pressure sensitive flexible diaphragm and thereby changes its displacement relative to the coil. Because the loop links the magnetic field of the coil, the mutual induction of the loop and the coil change with pressure, resulting in a change of the L-C resonant frequency with pressure. Such a shorted loop can be made only a few mils thick and of extreme light weight. The frequency versus displacement change can be made far greater with the shorted tuning loop than with any ferrite or magnetic tuning slug. Unlike the solid conductive slug or disk, the shorted loop with its through opening has minimal dissipative electrical losses and thus the Q of the resonant circuit can be maintained at a high level, comparable to that using a ferrite magnetic tuning slug. Unlike the ferrite magnetic slug, the shorted loop used as a tuning element continues to produce large frequency shifts with displacement at large axial displacements from the coil, and thereby significantly expands the device design possibilities as discussed below. The shorted loop can be easily embedded in a thin silicone diaphragm enabling the ultimate in fast dynamic response and enabling a nearly weightless tuning element attached to a webb-thin silicone valve or flow vane for the ultimate in pressure sensitivity. It has been built into a pressure sensor of less than 3 mm total thickness and used successfully in hydrocephalus shunting systems in children; an achievement which is far beyond the scope of any other previous designs. The improvement of the shorted loop tuning element has made the single diaphragm structure far simpler and more rugged than any previous designs and has greatly expanded the scope of possible devices that can be practically and economically fabricated. Its planar construction has made assembly extremely uncritical and trouble free, with none of the difficulties associated with cylindrical telescoping moving parts encountered with magnetic or conductive slug turned designs.

A fuller understanding of the invention design improvement and additional objects, advantages, and novel aspects of it will be gained from the following description, illustrative drawings, and various embodiments. FIGS. 1 and 5 describe the basic concept, physical principles, and physical bases of the advantages of the design improvement. FIGS. 6 through 21 illustrate the novel and unique advantages of the present design improvement in specific in vivo pressure sensing structures and also illustrate some unique new designs which are made practical and possible by the present design improvement.

DESCRIPTION OF THE DRAWINGS

FIG. 12 illustrates a variant of FIG. 11 with closed fluid coupling elements to each chamber.

FIG. 13 illustrates a fluid pressure sensor with external pressure source reference, again compactified by the shorted loop tuning element.

FIG. 14 illustrates a differential pressure sensor of FIG. 11 in parallel with a shunt valve.

FIG. 15 illustrates a combined pressure sensor and anti-syphon device which is made practical by the shorted loop improvement.

FIG. 16 illustrates a pressure sensitive device combined with volume change quantification which is made feasible by the shorted loop tuning improvement.

FIG. 17a illustrates a pressure sensitive telemetric flow valve, also made feasible by the shorted loop tuning improvement.

FIG. 17b is another variant of FIG. 17a.

Referring to FIG. 1, a thin-profile implantable differential pressure sensor is shown to illustrate the basic concept of tuning a passive telemetric L-C resonant circuit with a conductive shorted loop tuning element. The device of FIG. 1 also illustrates some of the advantages of compactness and simplicity of the present design improvement since this embodiment is a sensor of cerebrospinal fluid pressure that could be put in-line with a hydrocephalus shunt valve. Such valves and devices are typically used in infants and implanted between the scalp and the skull, so that an absolute minimum of thickness and size is a necessity. The fluid would enter the sensor by tube 29 and exit by tube 45. Within housing 5 and single flexible diaphragm 7 is a chamber inside which the fluid pressure is $P_{IN}$. When $P_{IN}$ exceeds $_{OUT}$, the pressure on the outer surface of 7, then 7 bulges upward. The objective of this and other similar sensors as described in the previous patent applications is to derive a detectable telemetric signal parameter outside the body which changes with the displacement of diaphragm 7 and thus changes with changes in $\Delta P = P_{IN} - P_{OUT}$. The methods of using such telemetric information to measure $P_{IN}$ itself are also described in the previous applications. In the example of FIG. 1, a passive L-C circuit with coil 12 and capacitor 13 is fixed within casing 5' which in turn is within housing 5, and the resonant frequency f of the L-C circuit is detected by a "grid-dip" type circuit outside the body (not shown).

The improvement of this patent application involves the way in which the resonant frequency f is changed with displacement of the diaphragm. It is claimed in the previous applications that by displacing a conductive material relative to coil 123 as 7 moves, frequency f is changed. In FIG. 1, a special geometry of the conductive material is disclosed in the form of a closed or shorted loop 14 embedded in the flexible diaphragm 7.

FIGS. 2, 3, and 4 illustrate the physical basis, preferred specifications, and some of the unique advantages of using this improvement of a shorted loop inductive tuning element in implanted in vivo pressure sensors. Referring to FIG. 2, because the magnetic fields of the coil 12 and loop 14 link each other, there is a mutual inductance between them, and the mutual inductance changes with the relative loop-coil displacement x. The effective inductance of the L-C circuit and thus the resonant frequency f is changed with changes in the mutual inductance and therefore with changes in x. Shown in FIG. 2 are magnetic field lines from a current in the coil 12. This field is most intense near to the coil and forms a dipole pattern at large distances. The frequency sensitivity df/dx is accordingly greatest when the loop is near to the coil and when the loop radius r is approximately the same as the coil radius R since for that condition the maximum number of field lines are cut per unit displacement in x.

The conductive shorted loop has a major advantage for an in vivo telemetric sensor over any solid conducting disk or slug tuning element in the sense that it allows the field lines to pass through it without surface distributed eddy current losses, whereas in the latter geometries there is significant energy dissipation and field attenuation within the tuning element itself. Such dissipation has the effect of lowering the Q of the L-C resonant circuit and drastically reducing the coupling to external electronics which detects the resonant frequency. The Q-value using the shorted loop, however, is very high and comparable to that using a magnetic tuning element. Note that the coil's magnetic field lines pass through the shorted loop to each an external detector with low attenuation; with a solid conductive disk in place of the loop the field lines would be strongly attenuated. A second advantage of the conductive loop versus conductive slug or disk is that the sensitivity df/dx is also higher over a wider range of x.

Figure 2:
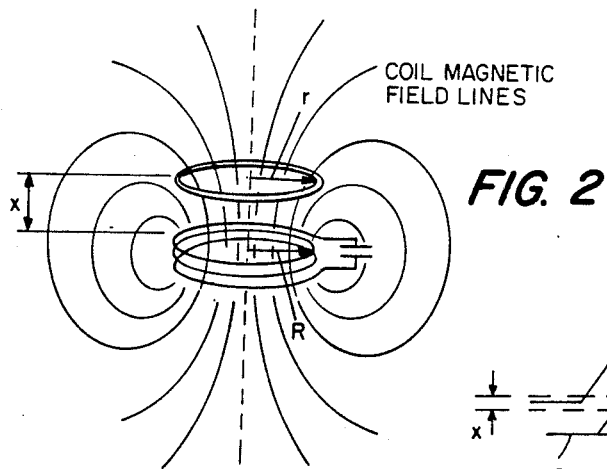
FIG. 2 shows the way in which the L-C circuit coil's magnetic field lines vary in space and the physical reason for the rapid distance dependence of the inductive coupling between the shorted loop and L-C circuit's coil.
Figure 3A:
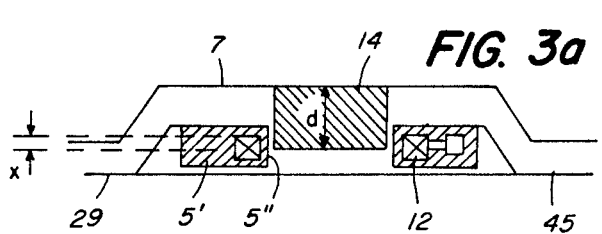
FIGS. 3a and 3b show typical relative dimensions of single diaphragm in vivo sensors involving permeability tuning of the L-C coil with a slug of magnetic material and inductive tuning of the L-C coil with a shorted loop, respectively. This illustrates superior constructional and dimensional aspects of the latter.
Figure 3B:
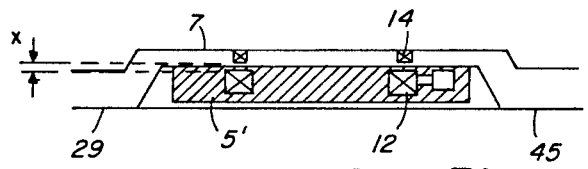
Figure 4:
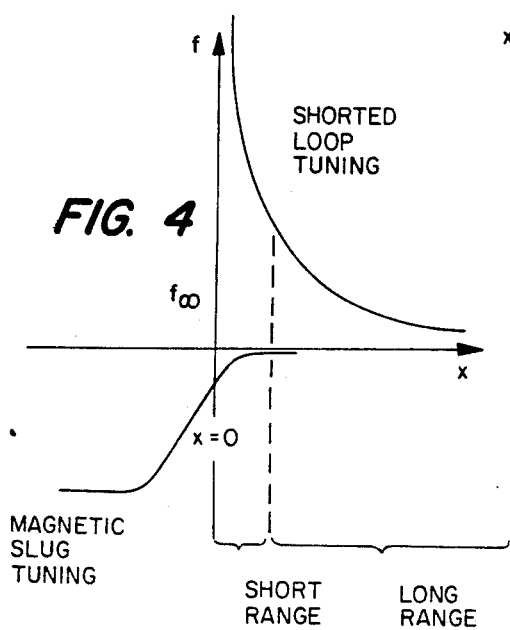
FIG. 4 illustrates the superior frequency sensitivity or df/dx characteristics of the shorted loop tuning over the magnetic slug tuning for the application of an in vivo pressure sensor. The graph is an experimentally determined plot of the L-C resonant frequency f as a function displacement x of the tuning element from the L-C coil. Note that the two graphs correspond to the configurations of FIGS. 3a and 3b and are plotted on the same f and x axis scales to show the relative df/dx variations. The axis scales are in arbitrary units.

The shorted conductive loop also has major advantages over the magnetic material tuning element for a clinically implanted device. Among the most important are extreme physical thinness and superior electronic sensitivity. In FIG. 3a is shown a typical configuration of a single diaphragm sensor with a magnetic tuning element, and in FIG. 3b is a single diaphragm sensor with shorted-loop tuning. Both configurations are drawn on the same scale, and their relative dimensions are chosen so that they are comparable in resonant Q-value and thus telemetric coupling. Thus, they are on an equal footing with respect to this specification, said specification being paramount for an in vivo telemetric pressure sensor. However, for the pressure sensitivity df/dx to be at all comparable, the magnetic element 14 in FIG. 3a must be at least of a thickness d=4 to 6 mm, which immediately makes the device unacceptably thick for use in infants. The displacement x in FIG. 3a is from the lower edge of the slug to the coil. The shorted-loop 14 in FIG. 3b on the other hand may be only 0.004" or 1/10 mm in thickness and still has a sensitivity df/dx which is 50 percent or more greater than the maximum achievable for a 4 mm thick magnetic tuning element. Beyond this the shorted-loop sensitivity remains strong even at long range, i.e., larger values of x, whereas the magnetic slug sensitivity is of far shorter range. This is illustrated in FIG. 4 which shows experimentally determined graphs of f versus x for the same coil geometry and the configuration of tuning elements of FIGS. 3a and 3b, x being defined as in FIGS. 2 and 3. Here $f\infty$ is the unperturbed L-C frequency when the tuning element is removed to infinite distance. At short range, i.e., x≃0, the slope df/dx for the shorted-loop is much greater in magnitude than df/dx for the magnetic slug, which means that the shorted-loop will produce a much more sensitive pressure sensor. At long range, i.e., larger x>0, df/dx continues to be significant in magnitude for the shorted-loop, but drops sharply to zero for the magnetic slug when the magnetic slug has ceased to penetrate the coil's outer margin at x=0. This means that the shorted-loop tuning can be used more effectively in designing quantitative in vivo pressure and volume sensors which involve large x excursions as described below.

Yet another advantage of the shorted-loop improvement is structural and constructional simplicity. Note in FIG. 3a that the magnetic tuning slug 14 must be inside the coil 12 to produce a large df/dx which means the coil must have a 5" in it and the magnetic slug 14 must be aligned properly in the hole to avoid contact friction. In the shorted loop design of FIG. 3b, no such problems arise since lack of precise coaxiallity of the loop 14 and the coil 12 does not affect the sensitivity df/dx. Note also that the large weight and volume of the magnetic tuning element make it unweildy to attach to a delicate diaphragm, make the response depend on the orientation of the sensor, and make the dynamic response slower in comparison to the planar and very light weight shorted-loop. The factor of the ultra light weight of the shorted-loop also makes possible ultrasensitive in vivo pressure sensing systems, as will be described below, which are impossible with the bulkier magnetic or conductive tuning slugs.

Still another crucial advantage of the design of FIG. 3b over that of FIG. 3a for in vivo pressure measurement of a bodily fluid such as brain cerebrospinal fluid or blood is reliability and workability over a long implantation time. As mentioned above, to achieve practical sensitivity, the magnetic slug 14 of FIG. 3a must penetrate the coil 12 and thus penetrate a hole 5" through the coil. Furthermore, the slug must be as large as possible to maximize df/dx which means that the clearance between slug 14 and hole 5' must be minimized. It is well known that coagulation of proteinous material in cerebrospinal fluid eventually forms a crust on the implant surfaces that it contacts, especially where flow of the fluid is slowest. This would be certain to occur between the slug walls and the hole in FIG. 3a, leading eventually to freezing up of the moving slug and diaphragm. On the contrary, in FIG. 3b, the fluid flow is maximum between the diaphragm 7 and the body 5', and there are no irregular or non-planar contours where friction from coagulum could cause failure. Here again, it is the ultimate simplicity of the moving part enabled by the shorted-loop tuning improvement which avoids this practical design problem.

Figure 5:
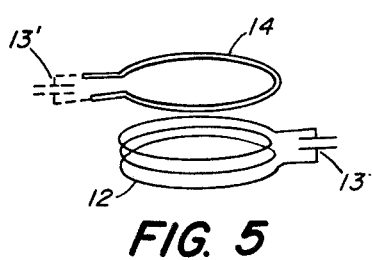
FIG. 5 shows a variant of the shorted loop induction tuning improvement where the loop is replaced by a second L-C resonant circuit, which is also a "shorted" loop in the sense of displacement currents in the second L-C circuit's capacitor.

It is understood that the present design improvement invention may have many variations. For example, the conductive shorted-loop may be varied in shape, viz circular, rectangular, etc., and so may the inductively coupled circuit coil. A multiturn conductive coil with closed ends could also be used in the same way as the single shorted-loop. The shorted-loop could be replaced by another resonant circuit, for example, the second L-C circuit shown in FIG. 5. The two L-C circuits are inductively coupled by the two coils, and the second one "pulls" the frequency of the other or detunes it as a function of their separation. The second capacitor 13' is shown dashed in FIG. 5 since, if the frequencies were high enough, the coil would in fact be open so long as the capacitive reactance of the coil itself and the gap between its open end were low enough for the reasonable inductive energy transfer between the two circuits. The conductive tuning element, such as the closed loop, could be integral with the diaphragm 7, for example, the diaphragm itself could be part metal or have an annular metal portion. The diaphragm itself, could have various geometries, viz convoluted diaphragms, cylindrical bellows, etc., with a metal annular portion.

Figure 1:
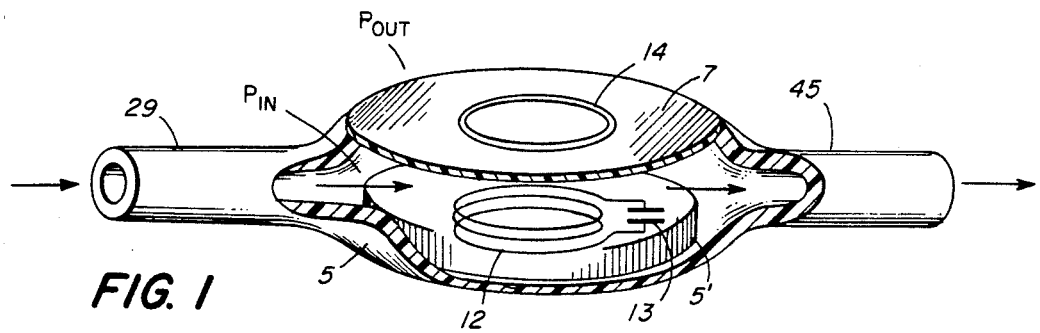
FIG. 1 shows a schematic cut-away view of a typical in vivo single diaphragm differential pressure sensor incorporating the conductive shorted loop design improvement and a passive L-C resonant circuit.

It is also understood that the L-C circuit which is tuned by the shorted-loop may be replaced by another type of circuit which has an inductor like coil 12 in FIG. 1 that is being tuned by the loop. For example, the circuit may include active elements, batteries, transistors, and integral circuits. It may be an L-R-C circuit or some other sort of resonant circuit. It may include a transmitter to transmit the resonant frequency or other response parameter to a nearby radio receiver outside the living body. It could even have direct wiring through the skin to external analysis circuitry. The circuit may have a characteristic response parameter which changes with circuit inductance other than resonance frequency, and this response parameter serves as an indicator of diaphragm movement. Examples would be the Q-value, phase response, or impedance of the circuit.

It is also understood that, as described in the previous patent applications, it is preferred to have a mechanical stop reference position of the flexible diaphragm and tuning element relative to the tuned circuit. However, there are some new applications which are made possible by the present design improvement which do not necessarily require such a reference position. As explained in the previous applications, the mechanical stop reference position enables the sensor to be zero calibrated in vivo and also the pressure calibration to be determined in vivo depending on the mode of uses, and thus it is an essential in certain contexts. If, however, only pressure variations or pressure-flow pulses need be seen, then the mechanical stop could be eliminated. As will be shown below, the present design improvement makes practical, very delicate, pressure gradient sensors in the form of ultra light-weight pressure vanes, and these might be the types of devices where the mechanical stop is not needed.

The device in FIGS. 6 through 21 illustrate further novel features of the present design improvement by means of specific embodiments.

Figure 6:
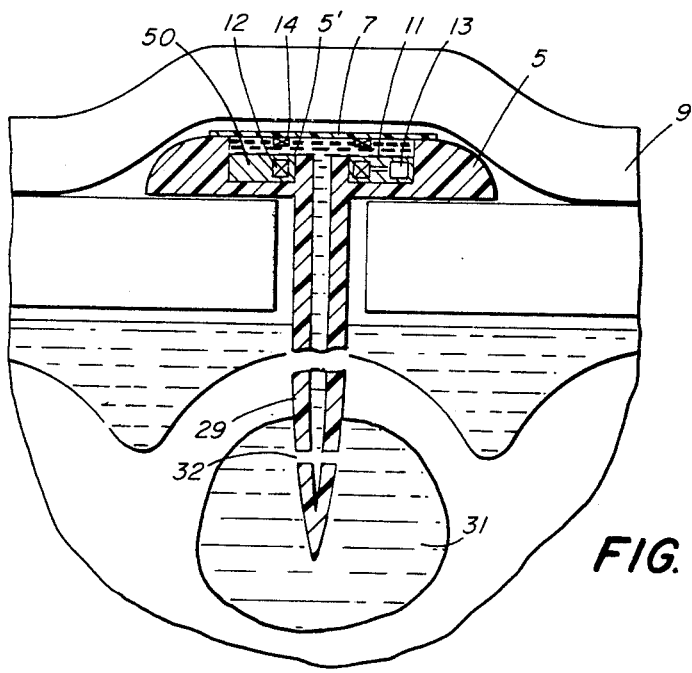
FIG. 6 illustrates a low profile single diaphragm differential pressure sensor for measuring a body fluid pressure and using the shorted loop tuning improvement.

FIG. 6 illustrates a single diaphragm, static, in vivo, fluid pressure sensor and indicates how thin and uncomplicated the improvement of the shorted-loop tuning of an L-C circuit makes such a device. Flexible diaphragm 7 is attached and fluid sealed to housing 5, and 5 and 7 form a chamber 50. An inlet tube 29 allows a body fluid 31 from a remote region, here cerebrospinal fluid 31 from the ventricle in the brain, to enter chamber 50 and communicate with diaphragm 7 on its inner side. Diaphragm 7 communicates on its outer side with intact scalp 9 above it and thereby with either atmospheric pressure outside the scalp or possibly with a pressure source outside 9 such as a cuff if pressure balancing is to be done. If intracranial pressure (ICP) of fluid 31 increases, then diaphragm 7 will bulge upward and change its position relative to housing 5 in an amount which depends on the amount above atmospheric pressure the ICP value attains. Inside 5 is a circuit housing 5' which contains a coil 12 and capacitor 13 which are part of the resonant circuit whose frequency can be detected by telemetry outside the body in standard ways such as by a "grid-dip" type oscillator.

Figure 7:
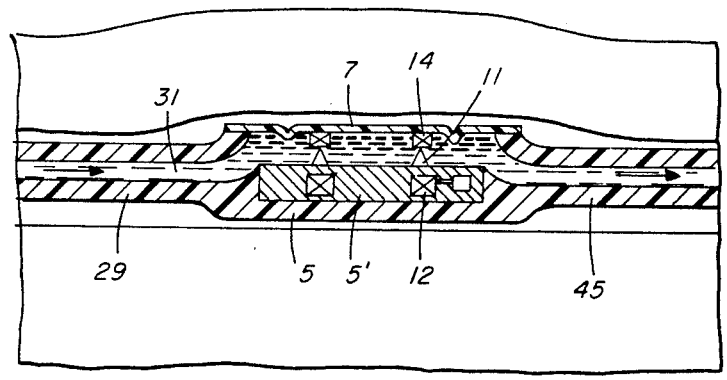
FIG. 7 illustrates a low profile in-line sensor of fluid pressure with inlet and outlet tubes and using the shorted loop tuning improvement.

FIG. 7 shows another variant of the single diaphragm sensor similar to that in FIG. 1 for in-line pressure sensing in a bodily fluid transport system, and shows how thin and simple the improvement enables such a device to be made. The housing 5 is flat-bottomed and contains the circuit housing 5' which may be an epoxied wafer which has embedded in it a resonant L-C circuit with inductor coil 12 and a parallel connected capacitor. The diaphragm 7 has attached to it the conductive shorted loop 14 and they move together under changes in pressure of fluid 31 that communicates with 7. Here a reference stop of 7 against shoulders 11 may be used corresponding to a given pressure relationship across the diaphragm 7, viz pressure balance. An entrance tube or port 29 and exit tube 45 carry fluid 31 into and out of the sensor. Such a device would be used in series with a fluid shunt system or a static fluid containing system. Thus the displacement of the flexible diaphragm 7 relative to the body 5 is a function of the pressure difference across 7. Again the position of 14 relative to circuit coil 12 determines the value of the resonant frequency that is measured telemetrically by electronics external to the body. The pressure versus displacement characteristic of 7 may be precalibrated or unknown depending on the mode of operation as discussed in references in the previous patent application.

Figure 8:
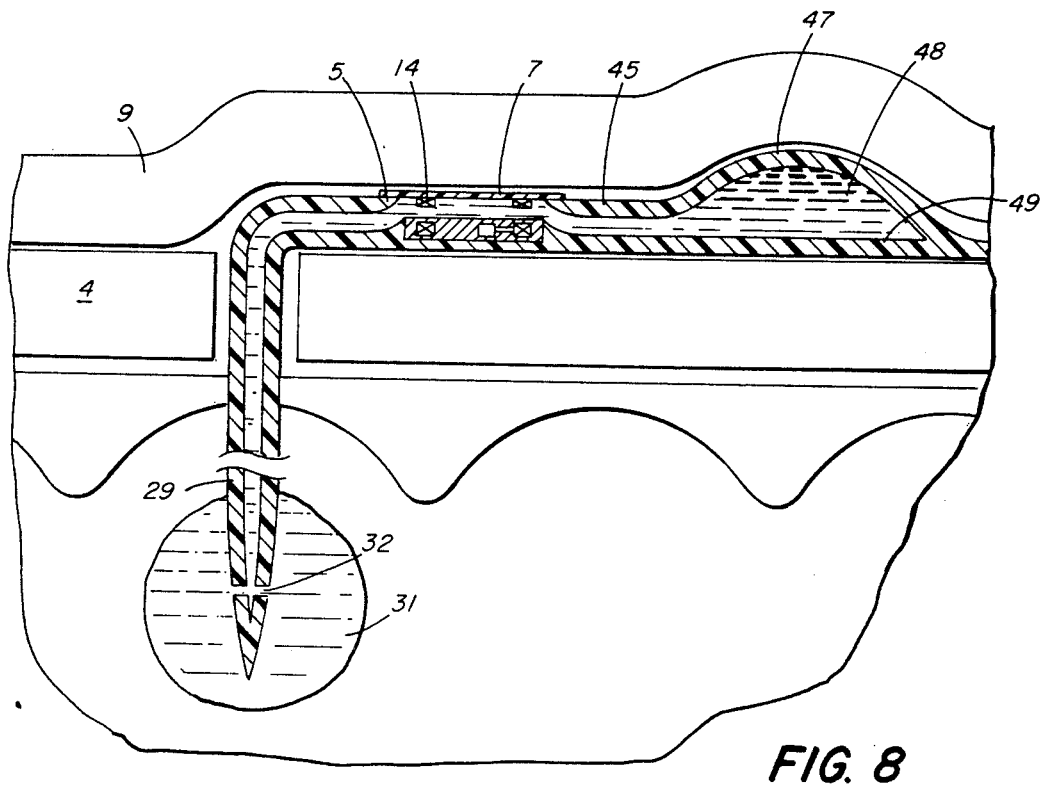
FIG. 8 illustrates a low-profile in-line pressure sensor as in FIG. 7 with ventricular catheter and fluid reservoir dome.

FIG. 8 shows another usage of the single diaphragm pressure sensor with the shorted-loop improvement similar to that of FIGS. 6 and 7 but where a fluid reservoir is connected in series with the system. Here the elements are the ventricular cathetor 29, which taps the fluid in the ventricle 31; the pressure sensor with its body 5 and flexible diaphragm 7, the connecting tube 45, and the domed reservoir that consists of a flexible domed top 47 and a flat bottom 49. This system allows intraventricular fluid pressure to be measured and also allows withdrawal or medication of that fluid by puncturing the dome 47 with a small hypodermic needle. Such a combination would be important for monitoring and treatment of patients with tumors, head injury, or hydrocephalus, and it is the compactness of the present improvement that makes it practical.

There is another novel variant of the system of FIG. 8 which has been used to measure the pressure versus volume compliance, or $dP/dV$, of the brain, a very important clinical parameter. This is done by designing the flexible domed fluid reservoir to have a predetermind volume $\Delta V$ so that when pressed digitally through the intact skin, on the flexible dome 47, it will displace the known volume $\Delta V$ of fluid back into the intracranial cavity. While doing this manipulation, the intracranial pressure P and pressure change $\Delta P$ can be monitored by the in-line pressure sensor and a curve of $\Delta P$ versus $\Delta V$ established or simply a single value of $dP/dV \simeq \Delta P/\Delta V$ at P determined. For this purpose, the volume of displacement of the reservoir is most conveniently established to be some integral number of cubic centimeters, viz $\Delta V = 1cc$ to simplify calculations. Thus, a series combination of a pressure sensor and a flexible quantitative-volume reservoir serves another unique clinical purpose. It is understood that to design such a quantitative volume reservoir, one could use specially shaped flexible domes 47 or specially contoured flexible bottom portions 49 so that when 47 is pressed from above, only the desired volume quantity will be ejected. Although not shown in FIG. 8, the inside of the bottom 49 might be dish-shaped or concave so that when flexible dome 47 is pushed digitally, the depressed dome 47 and shaped contour of 49 will mate in a well defined way thereby causing a known volume change $\Delta V$. Other designs are also possible involving convoluted diaphragms or domes 47 and different shaped reservoir bodies to accomplish the same desired effect. It is also notable that if the pressure sensor and quantitative volume fluid reservoir where not serially attached but instead physically separated, then the pressure-volume compliance could also be measured.

Figure 9:
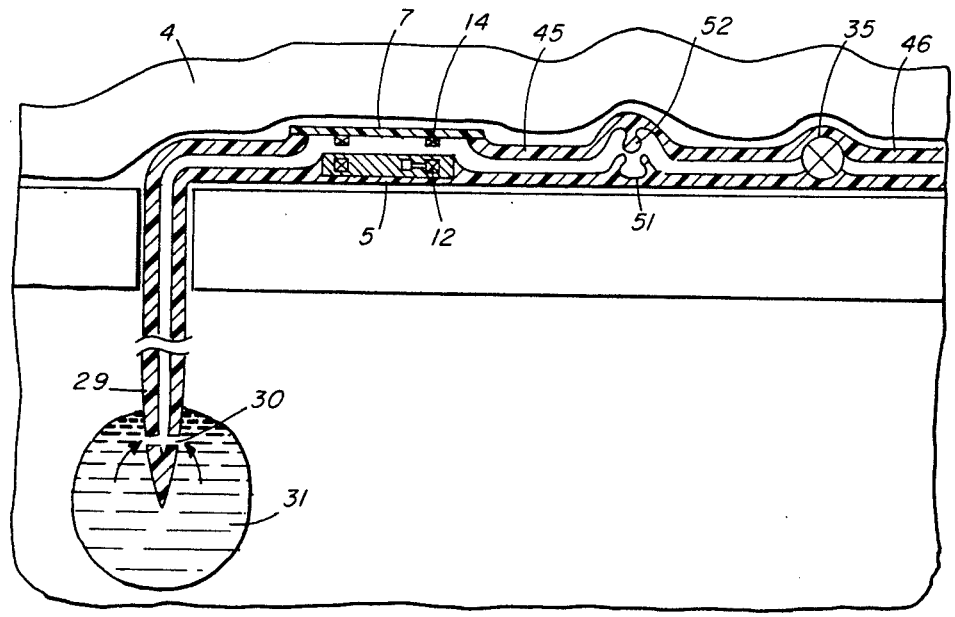
FIG. 9 illustrates a compact series connection of a catheter, shorted loop tuned pressure sensor, on-off switch, and shunt valve.

FIG. 9 shows yet another arrangement made practical by the shorted-loop improvement on a single diaphragm sensor, the sensor being connected in series with a ventricular fluid shunting system. Again cathetor 29 taps the ventricles, and the sensor measures the fluid pressure. Tube 45 connects to a pressure valve 35 which opens when the pressure is above a preset value and allows the fluid to shunt off in tube 46 to another region. As in FIGS. 1, 2, and 3, the thinness of 7 plus 14 is important to minimize the bulge of the sensor under the skin, and the simplicity of the integral conductor plus diaphragm moving element makes this modality practical and easily built. Such arrangements of this pressure sensor in-line with shunt valves has been shown to reveal unique clinical information on shunt valve function and flow of fluid in the system. For example, by measuring the pressure before the valve as in FIG. 9, it can be determined if the valve is opening and closing at the pressure that it should, and thus this enables the valve operation to be confirmed in vivo.

There is another novel feature shown in FIG. 9 which becomes possible with low profile sensor of FIG. 7 namely the use of an on-off vavle after the pressure sensor to access rate of fluid production. There are several possible designs for on-off valves; here a knob 52 on a flexible dome 53 which can be pressed from above and pushed into receptical 51 so as to close off the flow of fluid in the system. If this is done then the normal rate of production of fluid 31 in the brain will cause the pressure in the sensor to increase at a rate which depends on the natural fluid production rate and on the volume and compliance of the cranium. This rate of pressure build-up is important evidence as to the health of the natural production and absorption mechanisms, and thus the combination of the thin in-line pressure sensor, on-off valve, and shunt system is an important diagnostic device.

Figure 10:
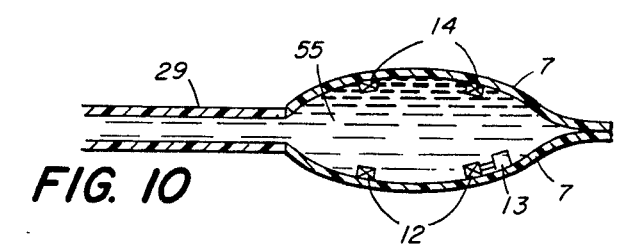
FIG. 10 illustrates a pillow-shaped telemetric sensor diaphragm, utilizing the ultra thin and light weight shorted loop concept.

FIG. 10 illustrates another conformation of the single diaphragm pressure sensor which is made possible by the extreme thinness of the shorted-loop tuning improvement. Instead of using a housing as in FIGS. 6, 7, 8, and 9, the diaphragm 7 itself is a flexible bag with an entrance port or tube 29 allowing a fluid 55 whose pressure is to be sensed to enter the bag. Embedded in one side of the bag wall is the primary circuit with its inductor 12 and, in this case, a capacitor 13. On the other wall is the shorted-loop tuning element 14. The fluid 51 may be a bodily fluid or may be a pressure communication fluid used to carry pressure from another diaphragm or pressure responsive means attached to the other end of tube 29. Thus, as FIG. 10 illustrates, a semi-rigid housing is not necessary. The bag of FIG. 10 may be placed under the skin to communicate with pressures outside the body or may be inserted into a bodily region where pressure is to be sensed. Several such sensing bags may be used in the same device. The bag may have a calibrated curve of pressure versus frequency (or any other characteristic parameter response of the circuitry embedded in it) or it may merely be a sensor of pressure changes. Note that the reference position might be the collapsed configuration of the bag with the inside surface of the opposing walls 7 touching each other so as to zero calibrate the device. Alternatively, the tuning element 14 can abut against the coil 12 to form the mechanical stop reference position. Similarly, shoulders 11 (see FIG. 7) can be used to stop the travel of the housing wall and coil 14. The exact shape of the bag may vary widely.

Figure 11:
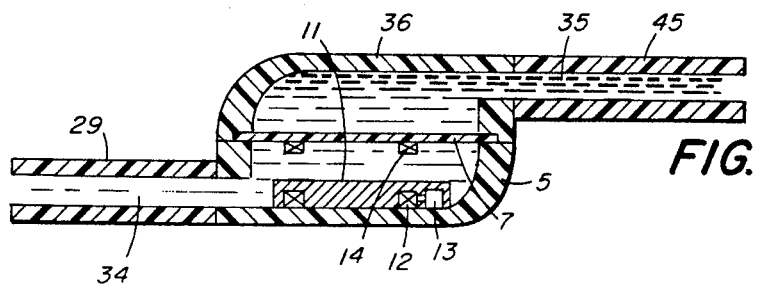
FIG. 11 illustrates a two chamber, single diaphragm pressure sensor, which takes great advantage from the ultra thin shorted loop tuning element.

FIG. 11 shows another type single diaphragm sensor which measures pressure differences or pressure variations between two regions, and which is made practical and simple by the light-weight, planar, shorted-loop tuning element. Inlet 29 carries a fluid 34 into one chamber formed by housing 5 and diaphragm 7 and inlet 45 carries a fluid 35 into a second chamber formed by 5 and 7. The diaphragm 7 moves in response to pressure difference changes of 34 and 35 and it carries the shorted-loop 14 that tunes the primary inductor 12 which is part of the circuit attached to the housing 5. The loop 14 may have a downward stop position against the surface 11 of the circuit housing 5' at a given pressure relationship between 34 and 35 on 7, or it may be free-floating. The portion 36 of the housing above the diaphragm may be flexible so that a pressure from above may force it to impinge on 7 and drive 7 to its stop against 11 for zero calibrating in vivo or for pressure calibrating in vivo. The sensor may be implanted so that 36 is in contact with exterior skin so that this maneuver is easily possible, or it may be implanted deeper in the body if pressure differences or variations are to be detected and zero calibrations are not to be made. The fluids 34 and 35 may be bodily fluids to separate regions or may be pressure coupling fluids acting as part of a larger device.

The last concept is illustrated in FIG. 12 where the sensing diaphragms 7' and 7" are sensing pressures in separated regions, and the fluids 34 and 35 transmit these pressures via tubes or channels to the sensor of the type of FIG. 6 which is located between 7' and 7". Diaphragm 7' could be located inside the cranium, whereas 7" could be between the scalp and the skull to communicate with atmospheric pressure or an externally applied pressure. Otherwise 7' and 7" could simply be located in two separated bodily regions to sense their pressure differences or any variations thereof.

FIG. 13 shows another variation of the use of a sensor like FIG. 6 where 29 carries a fluid that transmits a pressure to be sensed, either body fluid or transmission fluid as in FIG. 12. On the other side of 7, tube 45 connects via a break in the skin to an external pressure source; i.e., either atmospheric pressure or a controllable pressure source to carry out pressure balancing or zero calibrating. Note that a mechanical stop is clearly indicated for the motion of 7 in FIG. 13; this might correspond to the pressure balance point. Such stops could have been explicitly put in FIGS. 6, 8, 9, 10, 11, and 12 and were assumed possible in those examples. The tube 45 could also include wires connected to the circuit for direct external analysis of the characteristic detectable parameter rather than relying on a wireless telemetric method.

FIG. 14 shows a variant of the sensor of FIG. 11 which is arranged in parallel with a shunt valve 35 so that it senses quantitative pressure differences or merely variations of pressure across the shunt valve. Again in conjunction with a shunt valve, thinness of the sensor is essential and the shorted-loop tuning element is the ultimate in thinness and simplicity. Both pressure differences and variations are of interest, the first to learn precisely about opening and closing pressures in the shunt, and the second to detect physiologic or valve dynamics changes. A reference stop position at a given pressure relationship, a known pressure versus detectable parameter calibration, may be involved depending on the mode in which the device will be used.

FIG. 15 shows yet another adaptation of the single diaphragm sensor together with an anti-back flow or anti-syphon device where the shorted-loop tuning element makes an ultra thin device feasible. When the pressure in 29 is greater than that in 45, 7 will raise off the stop 11, and this will be sensed as before. When the pressure in 29 is less than that in 45, 7 will become seated on 11, occluding the passageway from 29 to 45 and thus preventing back flow of fluid between them. Alternatively, if 7 communicates with atmospheric pressure through the skin laying above it, then when pressure in 45 becomes less than atmospheric, 7 will close off the passageway preventing forward flow through the system. That is an anti-syphon action.

FIG. 16 shows yet another type of combined function device where the improvement of the shorted-loop tuning element makes the design practical and possible because of its long range sensitivity. It is an in vivo quantitative pressure and volume sensor. An inflatable chamber with a known total inflation volume $\Delta V$ includes a shorted-loop on the diaphragm 7 so that as 7 bulges upward because of an elevated pressure of fluid communicated to 7 through 29, the mutual induction of 14 to coil 12 changes with a resulting change in the detectable circuit parameter that is detected externally to the body. The relationship of volume change to change in the detectable parameter may be known or calibrated before implantation, and the relationship of the pressure change versus volume change or of the pressure change versus the detectable parameter change may be known or precalibrated depending on the application of the device. With such a device, for example, the $\Delta P/\Delta V$ curve or pressure-volume compliance of the brain may be determined, if 29 is sensing cerebrospinal fluid. The rate of change of volume with time as determined by the detectable parameter can yield information about brain fluid production. Again, the induction ring concept enables such a compact device to be made easily with a simple moving part.

FIG. 17a shows another unique use of the shorted-loop tuned pressure sensor where diaphragm 7 senses pressure differences associated with flow of fluid in the sensor which also functions as a valve system. Here the diaphragm 7 is attached only at an edge and can lift off an orifice 55 with a slight over pressure on the underside of 7. For example, entrance tube 29 allows fluid to communicate with the bottom of 7, and if the pressure in 29 is elevated above that in exit tube 45, 7 will lift up acting as a valve and allowing fluid to flow. Moving with 7 is the element 14 which tunes inductor 12 and changes the detectable parameter, viz resonant frequency, so that the valve action and associated flow is detectable. Dome 36 above 7 may be flexible so that if depressed it will push 7 and 14 to a stop over the orifice to zero the system or calibrate it in vivo if necessary. Thus, this acts as a combined pressure sensor and shunt valve. The circuit could be used to detect only motion of the valve and, therefore, serve as a monitor of valve operation. Alternatively, it can be considered as a flow indicator in the sense that it is a delicate pressure vane which moves with slight flow of fluid or associated pressure gradients. These different regimes are related and depend on the stiffness of 7 and whether it is designed to lift at a given pressure difference across it or whether it is extremely floppy and moves with the slightest pressure gradient. Assumed here is the possibility that 7 merely hangs in the path of fluid moving through the sensor so that both positive and negative pressure gradients will cause it to move. In such cases, it may not have a stop position or an associated orifice as in FIG. 17a. In such a case, the element 14 and diaphragm 7 act as a delicate "weather vane" or fluid flow detector. The extreme light weight of the shorted-loop design is a great advantage and makes such a device practical.

Figure 17B:
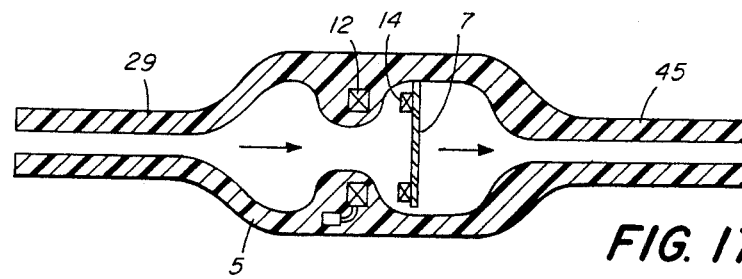

FIG. 17b is another variant of the device of FIG. 17a where housing 5 has a through opening with inlet port or tube 29 and outlet port or tube 45 so that fluid can flow through 5. The circuit inductor 12 may be fixed to the housing as shown so that it loops the through-opening. The flexible diaphragm 7 in this example is hanging from the "roof" of the housing inner wall so that as fluid passes through 5, the associated force of 7 would make it move, then causing the induction element 14 to change the inductance of 12. Here both positive or negative pressure gradients can be sensed, or variations of flow could be detected. The device could be precalibrated for inductance change of 12, or equivalent detectable parameter, versus flow rate and thus could be used as an absolute flow meter.

Figure 18:
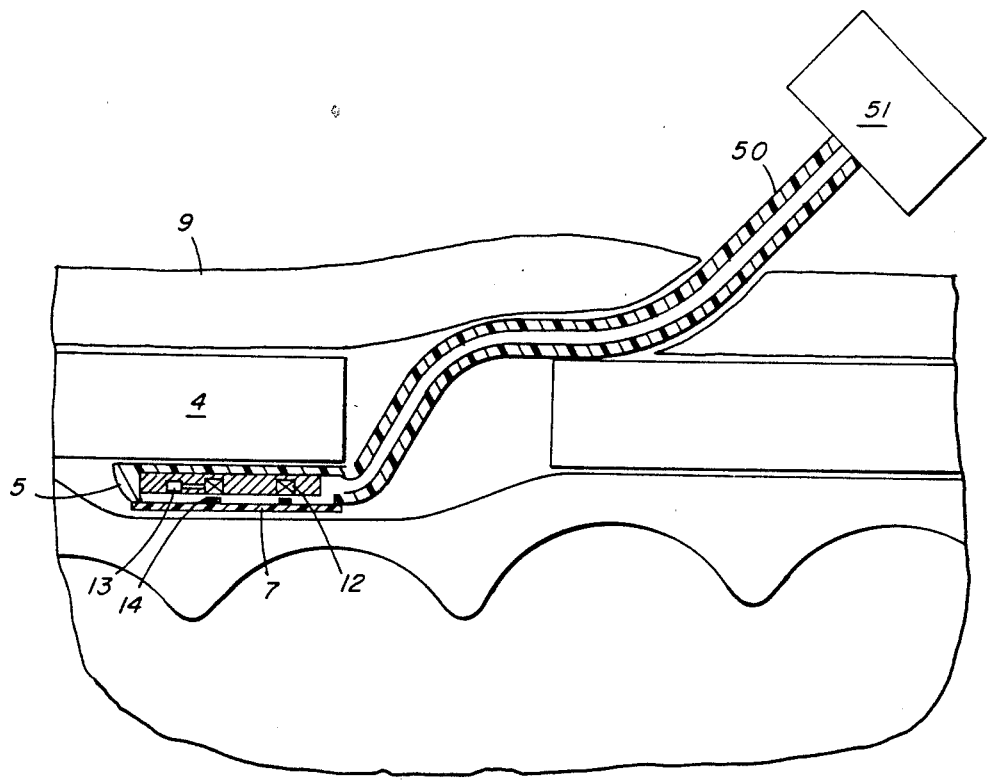
FIG. 18 illustrates a low profile externally coupled pressure balancing device with zero pressure detection telemetry.

FIG. 18 shows an externally coupled pressure source with an implanted shorted-loop tuned pressure sensor located between the skull 4 and over the brain. The pressure in external source 51 is controllable and communicates via tube 50 to the implanted chamber made up of housing 5 and diaphragm 7. When the pressure in 51 equals and just exceeds the brain pressure on 7, then 7 and conductive element 14 will move away from circuit inductor 14 and a resonant frequency change will be detected by electronic circuitry interrogating the implant from outside the body. This illustrates the thinness of the sensor element when the shorted-loop tuning conductor is used and how direct external pressure coupling can be used to measure a bodily pressure by a balancing method. It is analogous to the method of pressure-balancing in the previous applications except that there the pressure source is an air cuff applied directly to the sensor through the intact scalp.

Figure 19:
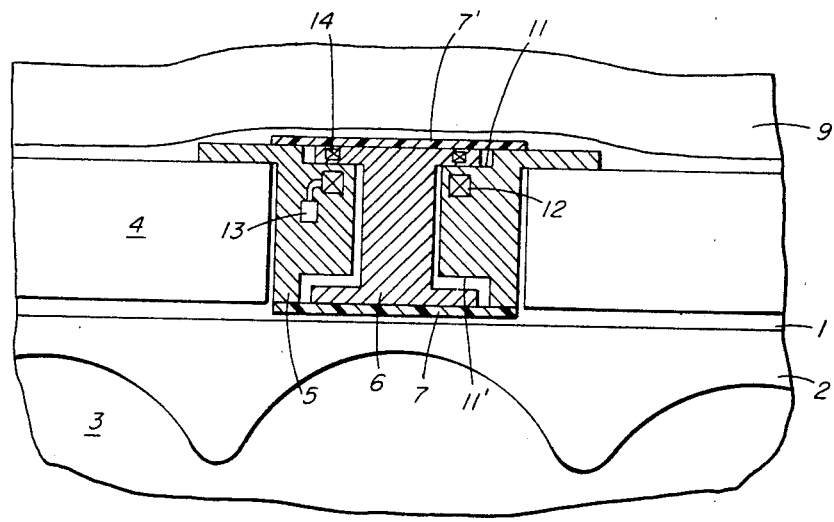
FIG. 19 illustrates a two diaphragm pressure sensor with rigid diaphragm coupling using the shorted loop tuning element.

FIG. 19 illustrates another class of sensor with two motion coupled diaphragms and an inductive shorted-loop tuning element included within it. The inner diaphragm 7 communicates directly with intracranial pressure and the outer diaphragm 7' mechanically communicates with external pressure by means of its contact and coplanarity with the intact scalp above it. The diaphragms are incompressibly motion-coupled by the rigid rod 6 which moves the body 5. The shorted-loop tuned pressure sensor is fixed in a burr hole in skull 4. This type of sensor is the same as in the previous patent applications. The increased intracranial pressure will displace 7, 6, and 7' upward by an amount depending on its increase above atmospheric pressure, the latter being approximately transmitted through the flexible scalp. The conductive induction current element, here a ring or coil, is fixed in the rod 6, and its displacement relative to inductive coil 12 produces the change in the resonant frequency which is detected outside the body and related to the pressure difference across the sensor.

In the mechanical motion coupling of FIG. 19, 6 could be replaced by other incompressible linkages or mechanisms, induction tuning element 14 could be integral with the diaphragm or integral with the coupling element 6, other type diaphragms could be used, such as rolling or convoluted diaphragms or cylindrical bellows, the diaphragms could be bag or pillow shaped, the diaphragms could be disposed other than at the ends of the housing opening so long as they can communicate with pressures in the desired regions; i.e., if fluid coupling or transmission is used, the diaphragms could be substantially inside the opening.

Figure 20:
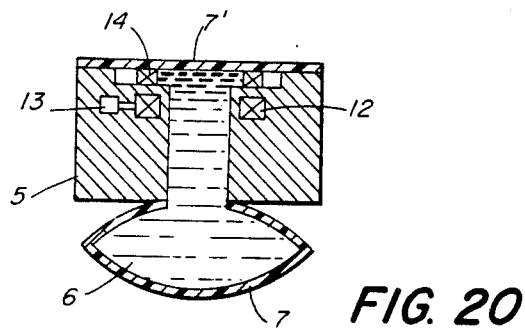
FIGS. 20 and 21 illustrate low profile two diaphragm pressure sensors with fluid diaphragm coupling and the shorted loop tuning improvement.
Figure 21:
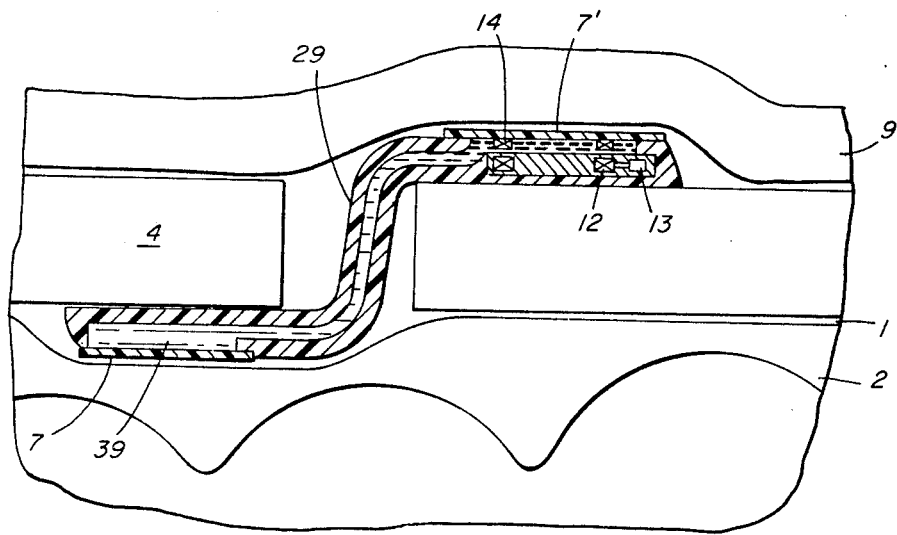

FIGS. 20 and 21 show variants of FIG. 19 in which fluid coupling is used instead of rigid coupling between 7 and 7'. In FIG. 15, 7 is a bag or pillow shaped diaphragm and communicates with some bodily pressure. Again in FIG. 20, 7' is shown coplanar with the upper housing opening, but it could be located inside the opening if it communicates with fluid. In FIG. 20, conductive ring 14 is attached to 7' and moves with it under pressure changes across the sensor, thereby changing the resonant frequency of circuit 12 and 13. The fluid 6 inside may be of various kinds; oil, ionic solutions, etc., depending on diaphragm material and permeability.

FIG. 21 is again a two diaphragm system and illustrates how the thinness of the shorted-loop design improvement can be important in this class of devices. A fluid 39 acts as coupling. As shown in FIG. 21, diaphragm 7 may be part of a separate chamber which communicates with pressure in a remote region. The chamber is connected by a tube to a second chamber which includes 7' and the telemetric electronics, in this case, the second chamber is above the skull 4 so that 7' communicates mechanically to an external force or pressure through the scalp 9. If the tube and chambers are of soft silicone, then a silicone fluid filling them may be used to transmit the pressures from 7 to 7'. An ionic solution could be used of such a concentration that would prevent osmotic diffusion of water and ions across 7 and 7'. Again, bag or pillow shaped diaphragms can be used instead of coplanar diaphragms; this would relieve the dependence on small volume changes of the transmission fluid between the diaphragms. Here a low profile of the resonant circuit and the conductive shorted loop 14 is important to reduce the bump under the scalp of the implant and resultant distortion of the communication of external pressures to the sensor.

It is also noted that more diaphragms may be used to communicate the differential pressures within the device.

Having described in detail various embodiments of the design improvement of my invention, it will now be apparent to those skilled in the art that numerous modifications can be made therein without departing from the scope of the invention as defined in the following claims.

What I claim and desire to secure by Letters Patent of the United States is:

1. An in vivo pressure sensor adapted for in vivo calibration, said sensor comprising:
 (a) a flexible housing defining a chamber therein;
 (b) inlet means allowing the entrance into said chamber of a bodily fluid the pressure of which is to be sensed when said sensor is implanted in the living body, said flexible housing being so adapted that when the sensor is implanted beneath the skin, at least a portion of the outside of said flexible housing is positioned to be adjacent to and facing an interior portion of skin whereby said outside portion of the housing is in mechanical pressure communication with the skin and whereby pressures external to the body and applied to the skin can be mechanically communicated across the skin to the outside of said flexible housing and so that changes in the differences in pressures inside said chamber and outside said housing will cause a distortion of said flexible housing;
 (c) mechanical stop means located within said flexible housing for preventing further distortion of the flexible housing when the pressure outside of the flexible housing equals or exceeds the pressure inside said chamber by a predetermined relationship;
 (d) means located within said flexible housing having a preselected parameter that is detectable by apparatus located outside the living body, said means having a preselected parameter being at least in part cooperatively connected to said flexible housing so that said preselected parameter will change with the movement of said flexible housing, said parameter being detectable at least when said flexible housing is at said mechanical stop means and said parameter changing upon at least a distortion of said flexible housing from said mechanical stop means whereby when said sensor is implanted beneath the skin, said flexible housing can be driven to said mechanical stop means by a pressure external to the living body applied to the skin adjacent to said sensor and said preselected parameter can be determined at said mechanical stop means after implantation, and whereby the magnitude of the external pressure applied to the skin required to drive said single diaphragm means to said mechanical stop means is a function of the pressure in said internal bodily region.

2. The sensor of claim 1 wherein said means having a preselected parameter comprises electronic circuit means with said preselected parameter being a characteristic response parameter of said electronic circuit means which is detectable by electromagnetic coupling to the electronic apparatus located external to said living body.

3. The sensor of claim 1 wherein said electronic circuit means is a resonant electronic circuit with an element of said resonant electronic circuit being at least in part cooperatively connected to said flexible housing so that a change of said distortion of said flexible housing will cause a change in said resonant frequency.

4. The sensor of claim 1 wherein said stop means prevents further distortion of said flexible housing when said pressure outside said flexible housing is equal to or greater than the pressure in said chamber.

5. An in vivo pressure sensor adapted for in vivo calilbration, said sensor comprising:
 (a) a flexible housing having means defining a chamber therein;
 (b) inlet means allowing the entrance into said chamber of a bodily fluid the pressure of which is to be sensed when said sensor is implanted in the living body, said flexible housing being so adapted that when the sensor is implanted beneath the skin, at least a portion of the outside of said flexible housing is positioned to be adjacent to and facing an interior portion of skin whereby said outside portion of the housing is in mechanical pressure communication with the skin and whereby pressures external to the body and applied to the skin can be mechanically communicated across the skin to the outside of said flexible housing so that changes in the difference in pressures inside said chamber and outside said housing will cause a distortion of said flexible housing;
 (c) mechanical stop means located within said flexible housing for preventing further distortion of the flexible housing when the pressure outside of the flexible housing equals or exceeds the pressure inside said chamber by a predetermined relationship;
 (d) means located within said flexible housing having a preselected, detectable variable parameter that is detectable by apparatus outside the living body, said preselected, detectable variable parameter changes as a known function of the pressures inside said chamber and outside said flexible housing; and whereby the sensor can be calibrated in vivo by driving said flexible housing into contact with said stop means by pressing on the skin adjacent to said sensor at which point the value of said preselected, detectable variable parameter can be determined, and whereby the change in said preselected, detectable variable parameter is a measure of the pressure of said bodily fluid.

6. The sensor of claim 5 wherein said preselected parameter comprises electronic circuit means with said preselected parameter being a characteristic response parameter of said electronic circuit means which is detectable by electromagnetic coupling to the electronic apparatus located external to said living body.

7. The sensor of claim 5 wherein said electronic circuit means is a resonant electronic circuit with an element of said resonant circuit being at least in part cooperatively connected to said flexible housing so that a movement of said distortion of said flexible housing will cause a change in said resonant frequency.

8. The sensor of claim 5 wherein said stop means prevents further distortion of said flexible housing when said pressure outside said flexible housing is equal to or greater than the pressure in said chamber.

9. An in vivo pressure detecting system comprising in combination:
 (a) a differential pressure sensor adapted for implantation in a living body and for in vivo calibration after implantation, said sensor comprising:
  (1) a housing which defines a chamber therein at least a portion of the wall of said housing being flexible so that changes in the pressure inside said chamber and outside said housing will cause movement of said flexible portion of said housing walls, said housing being adapted so that when implanted beneath the skin in the living body, said flexible portion of said housing wall can be placed in mechanical pressure communication with an interior portion of skin and whereby pressures external to the body can be communicated mechanically across the skin to said flexible portion of said housing wall;
  (2) inlet means to said chamber allowing the entrance into said chamber of a bodily fluid, the pressure of which is to be measured when the sensor is implanted in the body;
  (3) stop means within said housing adapted to make contact with, and thereby stop the movement of said flexible portion of said housing wall for a predetermined pressure relationship between pressures inside said chamber and outside said housing;
  (4) means within said housing having a preselected, detectable, variable parameter that is detectable by apparatus outside the living body, the preselected, detectable variable parameter changes as a known function of the pressures inside said chamber and outside said housing; and whereby the sensor can be calibrated in vivo by driving said flexible portion of wall into contact with said stop means by pressing on the skin adjacent to said sensor at which point the value of said preselected, detectable variable parameter can be determined, and whereby the change in said preselected, detectable variable parameter is a measure of the pressure of said bodily fluid;
 (b) means for detecting said value of said preselected, detectable variable parameter at said mechanical contact reference position and any variation therefrom when said sensor is implanted in a living body, said detecting means being located externally of the living body and without any connection to said sensor which requires a break in the skin of the living body.

* * * * *

UNITED STATES PATENT AND TRADEMARK OFFICE
CERTIFICATE OF CORRECTION

PATENT NO. : 4,385,636

DATED : May 31, 1983

INVENTOR(S) : ERIC R. COSMAN

It is certified that error appears in the above-identified patent and that said Letters Patent are hereby corrected as shown below:

Column 6, line 65, before "5'", insert -- hole --;

Column 10, line 25, after "natural" insert -- fluid --.

Signed and Sealed this

Seventeenth Day of April 1984

[SEAL]

Attest:

GERALD J. MOSSINGHOFF

Attesting Officer    Commissioner of Patents and Trademarks